United States Patent [19]

Vij

[11] Patent Number: 5,277,183
[45] Date of Patent: Jan. 11, 1994

[54] NMR LOCAL COIL FOR FOOT IMAGING

[75] Inventor: Kamal Vij, New Berlin, Wis.

[73] Assignee: Medical Advances, Inc., Wauwatosa, Wis.

[21] Appl. No.: 902,142

[22] Filed: Jun. 22, 1992

[51] Int. Cl.$^5$ .............................................. A61B 5/055
[52] U.S. Cl. .................................. 128/653.5; 324/318
[58] Field of Search ........................ 128/653.2, 653.5; 324/318, 322

[56] References Cited

U.S. PATENT DOCUMENTS

| | | | |
|---|---|---|---|
| 4,680,548 | 7/1987 | Edelstein et al. | 324/318 |
| 4,692,705 | 9/1987 | Hayes | 324/318 |
| 4,694,255 | 9/1987 | Hayes | 324/318 |
| 4,799,016 | 1/1989 | Rezvani | 324/318 |

Primary Examiner—Ruth S. Smith
Attorney, Agent, or Firm—Quarles & Brady

[57] ABSTRACT

A radio frequency coil for receiving NMR signals in the imaging of a human foot includes a bird cage structure of longitudinally separated loops joined by longitudinal segments. Some of the segments include transverse portions which define an appendant volume for receiving the toes of the foot when the foot is placed in the coil with the leg generally longitudinal and the toes extending transversely. The appendant volume allows the average radius of the coil to be decreased with a corresponding increase in signal-to-noise ratio without unduly affecting the homogeneity of the coil's reception pattern.

6 Claims, 2 Drawing Sheets

NMR LOCAL COIL FOR FOOT IMAGING

BACKGROUND OF THE INVENTION

1. Field of the Invention

The field of the invention is magnetic resonance imaging (MRI) and, in particular, local coils for use in receiving MRI signals.

2. Background Art

A. Magnetic Resonance Imaging

In MRI, a uniform magnetic field $B_0$ is applied to an imaged object along the z-axis of a Cartesian coordinate system the origin of which is approximately centered within the imaged object. The effect of the magnetic field $B_0$ is to align the object's nuclear spins along the z-axis.

In response to a radio frequency (RF) excitation signal of the proper frequency, oriented within the x-y plane, the nuclei precess about the z-axis at their Larmor frequencies according to the following equation:

$$\omega = \gamma B_0$$

where $\omega$ is the Larmor frequency, and $\gamma$ is the gyromagnetic ratio which is constant and a property of the particular nuclei.

Water, because of its relative abundance in biological tissue and the properties of its nuclei, is of principle concern in such imaging. The value of the gyromagnetic ratio $\gamma$ for water is 4.26 kHz/gauss and therefore, in a 1.5 Tesla polarizing magnetic field $B_0$, the resonant or Larmor frequency of water is approximately 63.9 MHz.

In a typical imaging sequence for an axial slice, the RF excitation signal is centered at the Larmor frequency $\omega$ and applied to the imaged object at the same time as a magnetic field gradient $G_z$ is applied. The gradient field $G_z$ causes only the nuclei in a slice through the object along an x-y plane, to have the resonant frequency $\omega$ and to be excited into resonance.

After the excitation of the nuclei in this slice, magnetic field gradients are applied along the x and y axes. The gradient along the x axis, $G_x$, causes the nuclei to precess at different frequencies depending on their position along the x axis, that is, $G_x$ spatially encodes the precessing nuclei by frequency. The y axis gradient, $G_y$, is incremented through a series of values and encodes the y position into the rate of change of phase of the precessing nuclei as a function of gradient amplitude, a process typically referred to as phase encoding.

A weak nuclear magnetic resonance generated by the precessing nuclei may be sensed by the RF coil and recorded as an NMR signal. From this NMR signal, a slice image may be derived according to well known reconstruction techniques. An overview of NMR image reconstruction is contained in the book "Magnetic Resonance Imaging, Principles and Applications" by D. N. Kean and M. A. Smith.

B. Local Coils

The quality of the image produced by MRI techniques is dependent, in part, on the strength of the NMR signal received from the precessing nuclei. For this reason, it is known to use an independent RF receiving coil placed in close proximity to the region of interest of the imaged object to improve the strength of this received signal. Such coils are termed "local coils" or "surface coils". The smaller area of the local coil permits it to accurately focus on NMR signals from the region of interest. Further, the RF energy of the field of such a local coil is concentrated in a smaller volume giving rise to improved signal-to-noise ratio in the acquired NMR signal.

The signal-to-noise ratio of the NMR signal may be further increased by orienting two coils at 90° angles about the imaged object so that each detects RF energy along one of a pair of mutually perpendicular axes. This technique is generally known as quadrature detection and the signals collected are termed quadrature signals.

The outputs of the quadrature coil pairs are combined so as to increase the strength of the received signal according to the simple sum of the output signals from the coils. The strength of the uncorrelated noise component of these signals, however, will increase only according to the square root of the sum of the squares of the noise components. As a result, the net signal-to-noise ratio of the combined quadrature signals increases by approximately $\sqrt{2}$ over the signal-to-noise ratio of the individual signal.

The quadrature orientation of the two coils introduces a 90° phase difference between the NMR signals detected by these coils. Therefore, combining the outputs from the two quadrature coils, to achieve the above described signal-to-noise ratio improvement, requires that one signal be shifted to have the same phase as the other signal so that the amplitudes of the signals simply add.

Such phase shifting and combining is typically accomplished by means of a hybrid network. Hybrid networks are four-port networks known in the art and having the property that when the four ports are properly terminated, energy input to two of the ports, with the proper relative phase angles, will be combined at one of the remaining two ports. The antenna coils are attached to two of the ports and the output lead is attached to a third port. The remaining uncommitted port is connected to a termination resistor.

As used herein, the term quadrature coil and quadrature signal, will refer to the detecting of the NMR signal along multiple axes and combining the signals so collected, with the appropriate phase shifts to produce a signal of improved signal-to-noise ratio.

C. Bird Cage Coils

One method of constructing a local coil is the "bird cage" construction in which two conductive loops are spaced apart along a common longitudinal axis and interconnected by a series of regularly spaced longitudinal conductors. The impedance of the loops and of the longitudinal conductors is adjusted so that the coil may be excited into resonance by a rotating transverse magnetic field at the Larmor frequency. A quadrature signal may be obtained by monitoring the current through two longitudinal conductors spaced at 90° around the periphery of the loops. Such coils are described in detail in U.S. Pat. Nos. 4,680,548, 4,692,705, 4,694,255 and 4,799,016, hereby incorporated by reference.

When a bird cage coil is employed as a local coil, the diameter of the loops and the length of the segments are reduced, so that the volume within the bird cage conforms closely to the imaged part. For the imaging of human limbs, and particularly for the imaging of the knee, the bird cage structure is dimensioned so that its cylindrical volume conforms closely to the outer surface of the leg.

In practice, the smallest practical radius of the bird cage is rarely realized for the reason that it is desired that the coil be suitable for imaging other members besides the knee, such as the foot. Imaging of the foot is preferably done with the foot in the anatomical position essentially perpendicular to the axis of the leg. The radial extension of the toes in this position limits how small the radius of the loops of the bird cage coil may be.

For this reason, the signal-to-noise ratio of bird cage coils intended for multipurpose imaging, including imaging of both the knee and foot, is significantly less than may be obtained for a coil not used for imaging the foot.

SUMMARY OF THE INVENTION

The present invention provides a local bird cage coil suitable for imaging both the knee and foot yet having a signal-to-noise ratio better than that which would be obtained from a bird cage coil having a diameter substantially equal to the length of the foot.

Generally, the bird cage coil of the present invention includes one or more connecting segments having offset portions connected by transverse links, perpendicular to the longitudinal axis of the coil, to provide a small area into which the toes of the foot may extend without increasing the radius of the coil generally. It has been determined that this small extension region does not unacceptably affect the homogeneity of the sensitivity of the interior of the coil.

More particularly, the coil of the present invention is made up of a pair of conductive loops separated along a common longitudinal axis and defining a generally cylindrical volume. Longitudinally-oriented first conductive segments conforming generally to the surface of this volume electrically interconnect the loop elements at points spaced along the periphery of each loop. At least one second conductive segment electrically interconnects the loops but includes transversely extending portions which define a second volume outside of the generally cylindrical volume, that second volume receiving the toes of the foot.

It is thus one object of the invention to provide a local bird cage coil for imaging the foot and having an improved signal-to-noise ratio over a bird cage coil with a diameter large enough to accommodate the full length of a transversely oriented foot. The transverse portions on the second conductive segment allow the segment to accommodate the toes of the foot for a small portion of its length while generally preserving the structure of a bird cage coil of smaller radius and improved signal-to-noise ratio for the remainder of its extent.

The points of attachment of the first and second conductive segments to the end loops may be equally spaced around the end loops. It is thus another object of the invention to provide a bird cage coil of decreased radius suitable for imaging the foot, but without reducing the number of segments or adjusting the spacing of the segments both of which may decrease coil homogeneity.

Other objects and advantages besides those discussed above will be apparent to those skilled in the art from the description of the preferred embodiment of the invention which follows. Thus, in the description, reference is made to the accompanying drawings, which form a part hereof, and which illustrate one example of the invention. Such example, however, is not exhaustive of the various alternative forms of the invention. Therefore, reference should be made to the claims which follow the description for determining the full scope of the invention.

DETAILED DESCRIPTION OF THE PREFERRED EMBODIMENT

Figure 1:
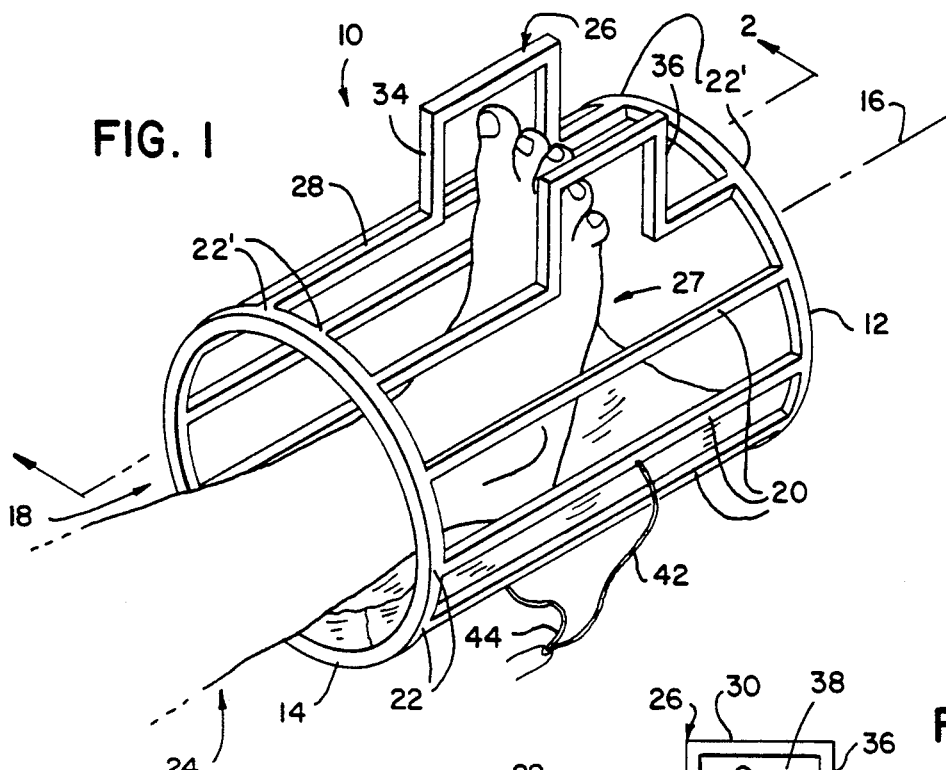
FIG. 1 is a perspective view of the coil of the present invention devoid of obscuring support structure and padding showing the placement of a foot within a volume of the coil.
Figure 2:
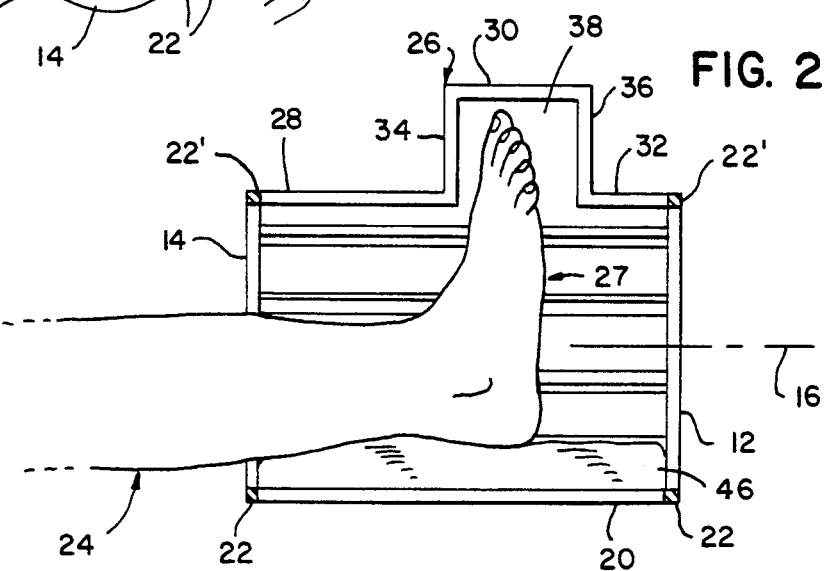
FIG. 2 is a cross-sectional view along lines 2—2 of FIG. 1 showing the configuration of one connecting segment which provides an appendant volume for the extension of the toes of the foot outside of the cylindrical volume defined by the end loops of the coil.

Referring to FIG. 1, a local coil 10 constructed according to the present invention includes a first and second conductive end ring 12 and 14 spaced apart along a common longitudinal axis 16 to define a generally cylindrical volume 18 between the rings 12 and 14. The rings are electrically connected by a plurality of conductive segments 20 which extend in a direction parallel to the longitudinal axis and connect to the end rings 12 and 14 at points 22 which are spaced at equal angles around the periphery of rings 12 and 14.

The diameter of the rings 12 and 14 is such as to receive a human leg 24 through one ring 14, but so that only a portion of a foot 27 associated with the leg 24 is received within the volume 18 when the length of the foot extends transversely to the longitudinal axis 16. The toes of the foot 27 protrude beyond the volume 18.

Two segments 26, also connecting the end rings 12 and 14 at points 22', include longitudinal portions 28, 30 and 32 separated by transverse portions 34 and 36. Longitudinal portion 28 connects at one end to ring 14 at point 22' and at its other end to a transverse inner end of transverse portion 34. The transverse outer end of transverse portion 34 connects to longitudinal portion 30. Longitudinal portion 30, at its other end, connects to the transverse outer end of transverse portion 36. The transverse inner end of transverse portion 36 connects to one end of longitudinal portion 32 which then connects to point 22' of ring 12.

Each of the longitudinal and transverse portions 28 through 36 are straight but the segments 26 formed of the portions 28 through 36 has an outwardly extending section to avoid the toes of the foot 27 and thus to create an appendant volume 38. The appendant volume 38 is outside of the cylindrical volume 18, defined by the segments 20 and the end rings 12 and 14, and generally encompasses the toes of the foot 27. The appendant volume 38 is located on three sides by segments 30, 34 and 36.

It will be understood that although longitudinal portions 28, 30 and 32 of segment 26 are all parallel to the longitudinal axis 16, that longitudinal section 30 in fact is positioned further from the longitudinal axis 16 than segments 28 and 32, and that the latter segments 28 and 32 are the same distance from the longitudinal axis 16 as are the segments 20.

Figure 3:
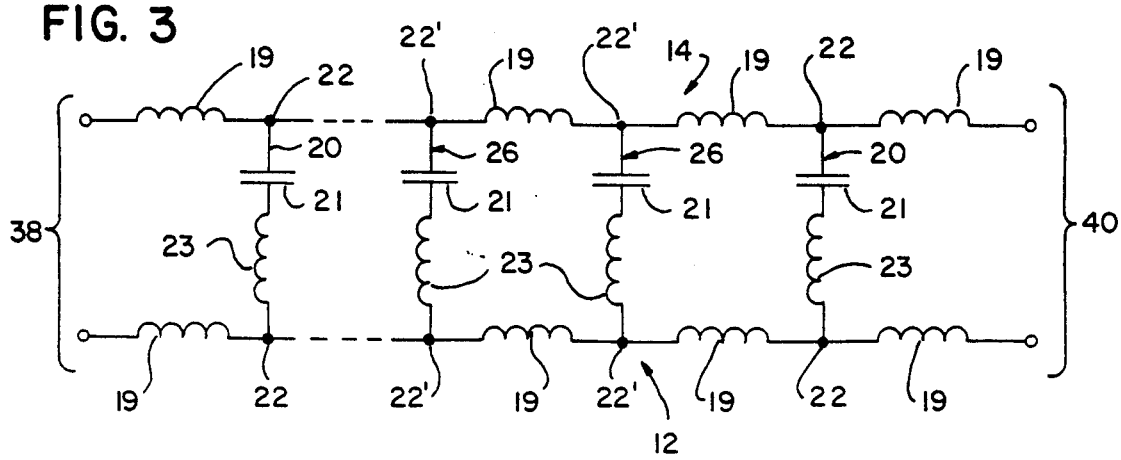
FIG. 3 is a schematic representation of the electrical characteristics of the coil of FIG. 1.

Referring to FIG. 3, the end rings 12 and 14 and the segments 20 and 26 are electrically conductive and electrically interconnected. Nevertheless, the impedance of each of these elements is not zero and must be adjusted to provide the necessary resonance of the local coil 10 near the Larmor frequency.

Referring to FIG. 3, the coil of FIG. 1 may be modeled as a ladder of interconnected inductances and capacitances representing the distributed impedance of the conductors forming the end rings 12 and 14 and the conductive segments 20 and 26.

In a so-called "low pass" configuration, the distributed inductance 19 of each ring 12 and 14, forming the "rails" of the ladder, is divided by the segments 20 and 26, forming the "rungs" of the ladder. The rungs have a net capacitive impedance provided by the insertion of small capacitors 21 along the length of the segments 20 or 26. The segments 20 and 26 also have an inductance 23 as a result of their physical extent, but this inductance 23, in the low pass configuration, is dominated by the added capacitance 21.

As modeled, it will be understood that this ladder resembles a delay line having input nodes 38 and output nodes 40, each being a corresponding pair of points on the rings 12 and 14, and that a voltage signal of a given frequency input at nodes 38 will be delayed in phase at nodes 40. Input and output nodes 38 and 40 are connected to each other in the formation of rings 12 and 14 and thus resonance can occur only when the values of the impedance of the end rings 12 and 14 and the segments 20 and 26 are such that a signal introduced at nodes 38 is phase shifted by a integer multiple of 360° at nodes 40. This phase shift accommodates the boundary conditions resulting from the connection together of nodes 38 and 40.

The selection of the values of the capacitors in the segments 20 and 26 will depend on the precise dimensions of the coil 10 but may be simply calculated for the Larmor frequency according to basic rules concerning electrical networks such as described. In distinction from a normal bird cage coil, however, because segments 26 are longer than segments 20, segments 26 will have a higher inductive value and thus will generally require greater values of accompanying capacitors 21. Specifically, for the embodiment shown, the value of the capacitors 21 will be selected according to the following formula:

$$X_{C21} = \frac{(X_{L19} + X_{L23}) - (X_{L23}\cos(\theta))}{1 - \cos(\theta)} \quad (1)$$

where $X_{C21}$ is the value of capacitance 21, $X_{L19}$ is the value of inductance 19, $X_{L23}$ is the value of inductance 23 and $\theta$ is the angular separation among adjacent segments 22 and 26. As noted, for segments 26 the value of $X_{L23}$ will generally be greater than the value of $X_{L23}$ for segments 22.

As will be understood to those of ordinary skill in the art, other configurations of the coil 10 may also be adopted including "high pass" or "band pass" configurations in which capacitances are introduced in the end rings 12 and 14 instead of or in addition to those introduced into the segments 20 and 26. Of importance only is that the resonance of the coil 10 be tuned to the desired Larmor frequency and that the current through each segment 20 or 26, at any given time be sinusoidally related to the angle of that segment about the longitudinal axis 16 as it is attached to that ring 12 or 14.

Referring again to FIG. 1, this condition of sinusoidal dependance of the current through each segment 20 and 26 on the angular position of that segment about the rings 12 and 14 allows quadrature signals to be obtained by coupling signal leads 42 and 44 to the current through any two segments 20 or 26 displaced by 90° with respect to each other about the longitudinal axis 16. This coupling may be by any of a variety of methods known in the art including use of a tapping capacitor or an inductive pickup in proximity to that segment.

The coil 10 is preferably constructed of a plastic body (not shown) having a low dielectric value, over which are arranged strips of conductive foil which form the rings 12 and 14 and conductive segments 20 and 26. The capacitors 21 are positioned across small cuts in the foil as needed. A foam cushion 46 (shown in FIG. 3) may be placed within the volume 18 of the coil to provide a support for the leg 24 and to move the region of interest of the foot 27 into the region of the coil 10 having most uniform sensitivity. Guide rails (not shown) such as are well understood in the art serve to position the coil 10 within the larger bore of the MRI magnet.

Figure 4:
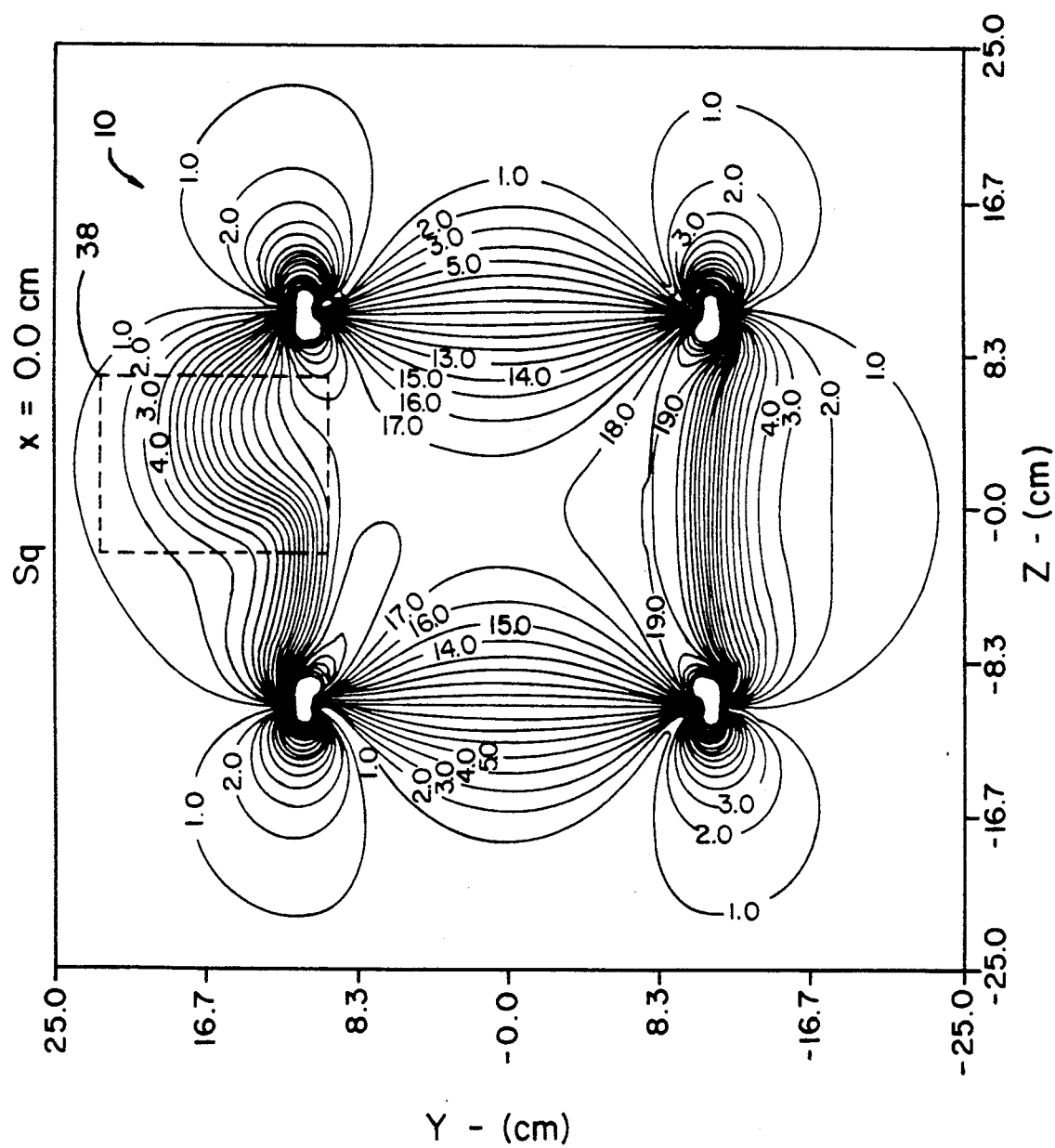
FIG. 4 is a chart mapping lines of equal sensitivity of the coil of FIG. 1 along the plane of FIG. 2.

Referring to FIG. 4, the deviation of the segments 26 does not significantly affect the uniformity of the sensitivity of the coil 10 in regions outside of the appendant volume 38 toward the center of the coil 10 where the region of interest of the foot 27 will be positioned.

The above description has been that of a preferred embodiment of the present invention. It will occur to those who practice the art that many modifications may be made without departing from the spirit and scope of the invention. For example, the rings need not be circular but may be slightly ellipsoidal to better accommodate the imaged limb. In order to apprise the public of the various embodiments that may fall within the scope of the invention, the following claims are made.

I claim:

1. An MRI radio frequency coil suitable for imaging portions of a human leg and foot comprising:

a pair of conductive loop elements separated along a common longitudinal axis for defining between them a generally cylindrical volume sized to receive a portion of the foot with the leg passing through one loop and lying generally along the longitudinal axis and the foot extending transversely with respect to the longitudinal axis with the foot's toes extending outside of the first volume;

a plurality of first conductive segments, longitudinally oriented and conforming generally to the surface of the cylindrical volume electrically interconnecting said loop elements at points spaced along the periphery of each of the loop elements; and at least one second conductive segment electrically interconnecting said loop elements, at points along the periphery of the loop elements, and having transversely extending portions defining an appendant volume outside of the first volume for receiving the toes.

2. The MRI radio frequency coil of claim 1 wherein the points are equally spaced along the periphery of the loop elements.

3. The MRI radio frequency coil of claim 1 wherein the loop elements are circular.

4. The MRI radio frequency coil of claim 1 wherein the appendant volume extends longitudinally for less than the longitudinal separation of the loop elements.

5. The MRI radio frequency coil of claim 1 including two conductive leads for receiving two MRI signals from the coil wherein the conductive leads are electrically coupled to two segments furthest removed from the at least one segment having transverse portions.

6. The MRI radio frequency coil of claim 1 wherein the at least one second segment having transverse portions is comprised of a series of straight segments.

* * * * *